Figure 1:
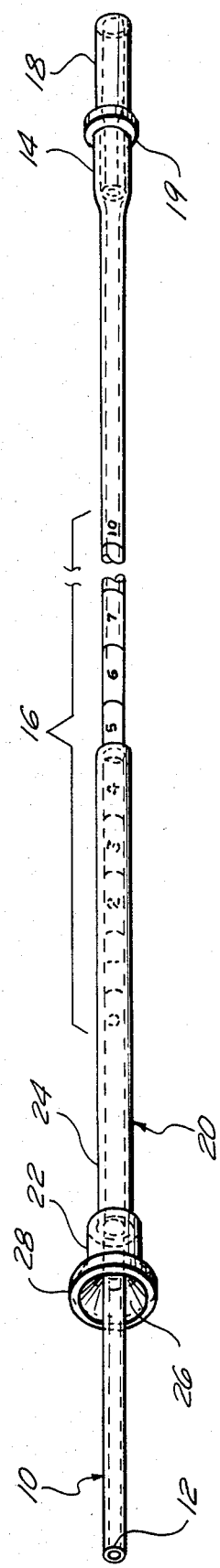

United States Patent [19]

Young

[11] Patent Number: 4,500,313
[45] Date of Patent: Feb. 19, 1985

[54] URETHRAL CATHETER

[75] Inventor: David E. Young, Watlington, England

[73] Assignee: Protectair Limited, Watlington, England

[21] Appl. No.: 461,564

[22] Filed: Jan. 27, 1983

[51] Int. Cl.³ .............................................. A61B 5/10
[52] U.S. Cl. ..................................... 604/280; 128/774
[58] Field of Search ................. 604/171, 93, 117, 264, 604/278, 280, 170; 128/768, 774, 778

[56] References Cited

U.S. PATENT DOCUMENTS 3,796,211  3/1974  Kohl .............................. 604/171 X
4,224,951  9/1980  Hasson .............................. 128/778

FOREIGN PATENT DOCUMENTS 7902339  9/1980  Netherlands ........................ 128/778

Primary Examiner—Stephen C. Pellegrino
Attorney, Agent, or Firm—James & Franklin

[57] ABSTRACT

The catheter includes an inner tubular member and an outer sleeve member into which the inner tubular member is freely movably received. The inner tubular member has a section with calibrated markings. The calibrated section is spaced from the end adapted to be received in the urethra, by a distance equal to the length of the outer sleeve member. The outer sleeve member has an outwardly flared end adapted to be situated adjacent the external urethral meatus. The non-flared end of the sleeve member is used as a pointer against the calibrated markings to determine the length of the urethra.

7 Claims, 2 Drawing Figures

U.S. Patent  Feb. 19, 1985  4,500,313

ÜRETHRAL CATHETER

The present invention relates to medical instruments and, more particularly, to an improved urethral catheter primarily designed for use in urodynamic procedures.

A catheter is a slender tube made of rigid or flexible material designed to be inserted into a body cavity for distending a passage or drawing off fluid. For example, a catheter may be inserted into the urethra and used to draw urine from the bladder.

During certain urodynamic procedures, a catheter is inserted into the urethra and, thereafter, moved within the urethra until the end thereof is aligned with the neck or opening in the bladder. The depth of insertion may be measured to ascertain the effective length of the urethra.

In certain procedures for measuring incontinence in women, a catheter equipped with calibration markings at the insertion end is utilized. The catheter is moved up the urethra until fluid begins to flow through the tube. This position identifies the bladder neck and the urethral length can be read from the calibration marks.

Since the catheter is handled during this procedure, during insertion and while the catheter is moved up and down the urethra, the sterility of the catheter is often compromised. Accordingly, the risk of infection is present.

Moreover, it is often difficult to obtain an accurate reading from the calibration marks on the catheter when same are adjacent the insertion end of the catheter. This is because of the flexibility of the external urethral meatus and because the view of the calibrated markings may be obscured by the labia.

The above noted disadvantages are overcome by the improved urethral catheter of the present invention. As described in detail below, the improved urethral catheter of the present invention includes an outer sleeve, in the form of a tubular member, into which the inner tubular member is freely movably received. Thus, the person performing the catheterization need not touch or come into contact with the portion of the inner tubular member which is inserted into the urethra. Consequently, the sterility of the portion of the inner tubular member which is inserted into the urethra is maintained.

Accurately measuring the urethral length is facilitated by spacing the calibrated portion of the inner tube from the insertion end by a distance equal to the length of the outer sleeve. The outer sleeve is provided with a flared end adapted to be positioned against the external urethral meatus. After the inner tubular member is positioned within the urethra, the measurement is read by the position of the non-flared end of the sleeve along the calibrated section of the inner tubular member. Consequently, the measurement can be taken with increased accuracy and ease.

It is, therefore, a prime object of the present invention to provide an improved urethral catheter capable of substantially reducing the risk of injection during urodynamic procedures by maintaining the sterility of the portion thereof inserted into the urethra.

It is another object of the present invention to provide an improved urethral catheter wherein measurements of distance can be performed with increased accuracy and ease.

It is another object of the present invention to provide an improved urethral catheter which is simple in design, easy to use, and inexpensive to manufacture.

In accordance with the present invention, a catheter is provided comprising an inner tubular member having an end adapted to be received in the urethra and an outer sleeve member into which the inner tubular member is freely movably received. The outer sleeve member has an outwardly flared end adapted to be situated adjacent the external urethra meatus.

The inner tubular member comprises a section, spaced from the inner tubular member end, comprising calibration markings thereon. The length of the outer sleeve member is substantially equal to the distance between the inner tubular member end and the calibrated section.

The flared end of the outer sleeve member comprises a part including first and second sections. The first section has a substantially cylindrical shape and is affixed to the tubular portion of the outer sleeve member. The second section has a substantially conical portion and is affixed to the first section. The second section also comprises a substantially cylindrical portion at the wide end of the conical portion.

Means for operably engaging a drain tube or the like is located at the end of the inner tubular member opposite the end adapted to be inserted in the urethra. The engaging means comprises means adapted to be inserted into and frictionally engage the opening in the tube. The engaging means also includes means for preventing the insertion of the frictionally engaging means into the opening in the tube beyond a given length.

Figure 2:
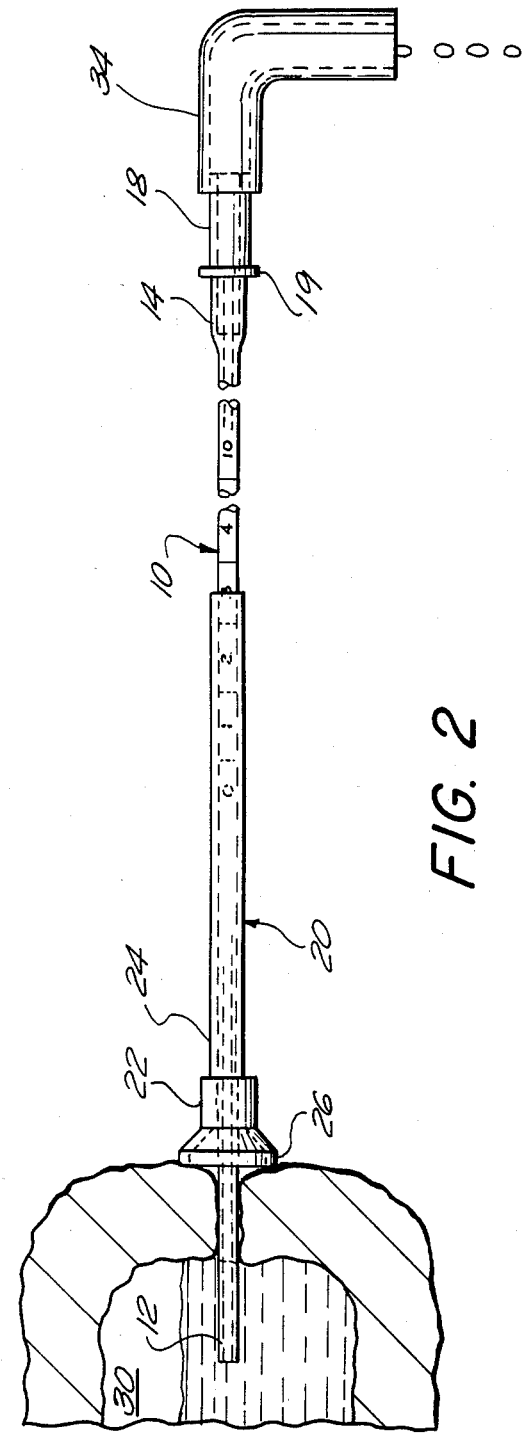

To these and such other objects which may hereinafter appear, the present invention relates to an improved urethral catheter as described in the following specification and recited in the annexed claims, taken together with the accompanying drawings wherein like numerals refer to like parts and in which:

FIG. 1 is a perspective view of the improved urethral catheter of the present invention; and FIG. 2 is a schematic drawing illustrating the method of use of the improved urethral catheter of the present invention.

As illustrated in FIG. 1, the improved urethral catheter of the present invention includes an inner tubular member 10, preferably composed of flexible plastic or the like. Inner tubular member 10 has an end 12 adapted to be inserted into the urethra and an end 14 adapted to be affixed to a drain tube or the like. Approximately mid-way between ends 12 and 14 is a section 16 which contains calibration markings, shown here as the numbers 1–10. End 14 of tubular member A is provided with a means for frictionally engaging the opening of a drain tube (not shown in this Figure). This engaging means includes a hollow substantially cylindrical section 18 having an outer diameter approximately equal to the inner diameter of the drain tube, into which it is adapted to be received. Limit means 19, in the form of a flange or annular member, is situated on section 18 so as to limit the distance which section 18 can be inserted into the drain tube.

Inner tubular member 10 is freely movably received within an outer sleeve member 20, preferably composed of a plastic somewhat more rigid than the plastic of which inner tubular member 10 is composed. Affixed to one end of sleeve 20 is an outwardly or radially flared part. The flared part includes a generally cylindrical section 22 affixed to the tubular part 24 of sleeve 20 and a substantially conical portion 26 having a hollow or concave face or interior and a generally cylindrical rim 28.

The method of use of the improved urethral catheter of the present invention is illustrated in FIG. 2 wherein the cavity at the left side of the drawing labelled 30 is intended to schematically represent the bladder and the channel connected thereto and labelled 32 schematically represents the urethra. When a urodynamic procedure must be performed which entails the insertion of a catheter into the bladder, the flared portion 26 of sleeve 20 is held by the person performing the catherization adjacent to the external urethral meatus while the labia are held apart. The end 12 of the inner tubular member 10 is then inserted into the urethra and pushed into the bladder by feeding it into the non-flared end of sleeve 20.

If a Fluid Bridge (Flow) test is being performed, end 12 of the inner tubular member is inserted into the urethra such that fluid begins to flow through the inner tubular member 10 and the drain tube 34 attached to end 14 thereof. End 12 is then slowly withdrawn until fluid ceases to flow through the tube. At this point, the end 12 of inner tubular member 10 is positioned at the bladder neck. The length of the urethra is then read from the calibration marks along section 16 of inner tubular member 10 by using the non-flared end of sleeve 20 as a pointer against the calibrated markings. For example, if one were reading the markings of the catheter shown in FIG. 1, it would read approximately $4\frac{1}{2}$ cm.

As now will be appreciated, the improved urethral catheter of the present invention has several major advantages over conventional catheters of this type. First, the hands of the person performing the test never need come into contact with the sterile inner tubular member, thereby substantially reducing the risk of infection. Second, the improved urethral catheter of the present invention provides a more accurate reading and provides a calibration scale which is much more easily visually accessible. In addition, the improved urethral catheter of the present invention has a very simple design, is easy to use, and is inexpensive to manufacture.

While only a single preferred embodiment of the present invention has been disclosed for purposes of illustration, it is obvious that many modifications and variations could be made thereto. It is intended to cover all of these variations and modifications which fall within the scope of the present invention, as defined by the following claims

I claim:

1. A catheter comprising an inner tubular member having an end portion with an opening, said end portion being adapted to be received in the urethra and an outer sleeve member into which said inner tubular member is freely movably received, said outer sleeve member having an enlarged end adapted to be situated adjacent the external urethral meatus, said inner tubular member comprising a section comprising calibration markings thereon, said calibration section being spaced from said opening in said end portion a distance substantially equal to the length of said outer tubular member.

2. The catheter of claim 1, wherein said sleeve member has a tubular portion and wherein said flared end comprises a part comprising first and second sections, said first section having a substantially cylindrical shape and being affixed to said tubular portion of said outer sleeve member, said second section having a substantially conical portion and being affixed to said first section.

3. The catheter of claim 2, wherein said second section further comprises a substantially cylindrical rim on said conical portion.

4. The catheter of claim 1, further comprising means for operably engaging a tube, said engaging means being located at the other end of said inner tubular member.

5. The catheter of claim 4, wherein said engaging means comprises means adapted to be inserted into and frictionally engage the opening in a tube.

6. The catheter of claim 5, wherein said engaging means comprises means for limiting insertion of said frictional engaging means into the opening in the tube beyond a given distance.

7. The catheter of claim 1, wherein said outer sleeve member comprises a tubular portion.

* * * * *